(12) United States Patent
Watson et al.

(10) Patent No.: US 8,808,157 B2
(45) Date of Patent: Aug. 19, 2014

(54) DEVICES FOR ASSEMBLING STRANDS COMPRISING RADIOACTIVE SEEDS

(75) Inventors: Breese J. Watson, Highland Heights, OH (US); Michael W. Drobnik, Downers Grove, IL (US); Jeffrey Neaves, Duluth, GA (US); Robert Brownwell, Jr., Decatur, GA (US); Erick Rios, Atlanta, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1098 days.

(21) Appl. No.: 11/771,741

(22) Filed: Jun. 29, 2007

(65) Prior Publication Data

US 2008/0161635 A1    Jul. 3, 2008

Related U.S. Application Data

(60) Provisional application No. 60/806,456, filed on Jun. 30, 2006, provisional application No. 60/806,457, filed on Jun. 30, 2006.

(51) Int. Cl.
*A61M 36/12* (2006.01)

(52) U.S. Cl.
USPC ............................................................ 600/7

(58) Field of Classification Search
CPC ............ A61N 5/10; A61N 2005/1009; A61N 2005/01; A61M 37/0069
USPC .................................. 600/1–8; 604/187–243
See application file for complete search history.

(56) References Cited

U.S. PATENT DOCUMENTS

| | | | | |
|---|---|---|---|---|
| 5,851,172 | A * | 12/1998 | Bueche et al. | 600/7 |
| 6,010,446 | A | 1/2000 | Grimm | |
| 6,035,603 | A * | 3/2000 | Focke et al. | 53/52 |
| 6,213,932 | B1 * | 4/2001 | Schmidt | 600/7 |
| 6,261,219 | B1 | 7/2001 | Meloul et al. | |
| 6,537,192 | B1 * | 3/2003 | Elliott et al. | 600/1 |
| 6,595,908 | B2 * | 7/2003 | Loffler et al. | 600/7 |
| 6,626,817 | B2 * | 9/2003 | Luth | 600/7 |
| 6,669,622 | B2 | 12/2003 | Reed et al. | |
| 6,730,013 | B1 * | 5/2004 | Shank et al. | 600/7 |
| 6,837,844 | B1 * | 1/2005 | Ellard et al. | 600/7 |
| 6,949,064 | B2 | 9/2005 | Lowery et al. | |

(Continued)

FOREIGN PATENT DOCUMENTS

WO    2009005528 A1    1/2009

OTHER PUBLICATIONS

JP 2010-514742 filed Jul. 18, 2007 First Office Action dated Apr. 10, 2012.

(Continued)

*Primary Examiner* — Catherine B Kuhlman
(74) *Attorney, Agent, or Firm* — Rutan & Tucker LLP

(57) ABSTRACT

A cartridge may include a housing configured to contain a plurality of like items and a track inside the housing. The track extends in a first direction, and a plunger may be slidable along the track in the first direction and configured to urge the items toward a first end of the housing. The cartridge may include a gate attached to the housing. The gate may be movable between a first position preventing the items from being removed from the housing and a second position allowing one of the items to be removed from the housing. The gate may be configured to remove the one item from being urged by the plunger.

16 Claims, 9 Drawing Sheets

(56) References Cited

U.S. PATENT DOCUMENTS

| | | |
|---|---|---|
| 6,969,344 B2 | 11/2005 | Drobnik et al. |
| 2001/0053870 A1* | 12/2001 | Loffler et al. .................... 600/7 |
| 2002/0058854 A1* | 5/2002 | Reed et al. ........................ 600/7 |
| 2003/0028067 A1* | 2/2003 | Tarone et al. .................... 600/1 |
| 2004/0077919 A1 | 4/2004 | Drobnik et al. |
| 2004/0162458 A1* | 8/2004 | Green et al. ..................... 600/7 |

OTHER PUBLICATIONS

JP 2010-514742 filed Jul. 18, 2007 Second Office Action dated Oct. 2, 2012.

PCT/US2007/073773 filed Jul. 18, 2007 International Preliminary Report on Patentability and Written Opinion dated Oct. 9, 2008.

PCT/US2007/073773 filed Jul. 18, 2007 International Search Report dated Oct. 9, 2008.

\* cited by examiner

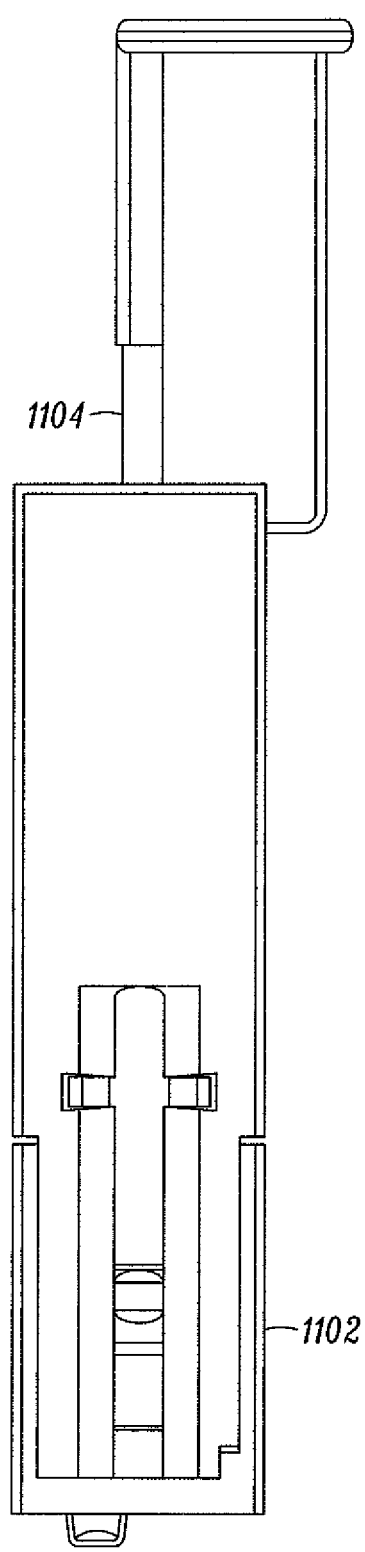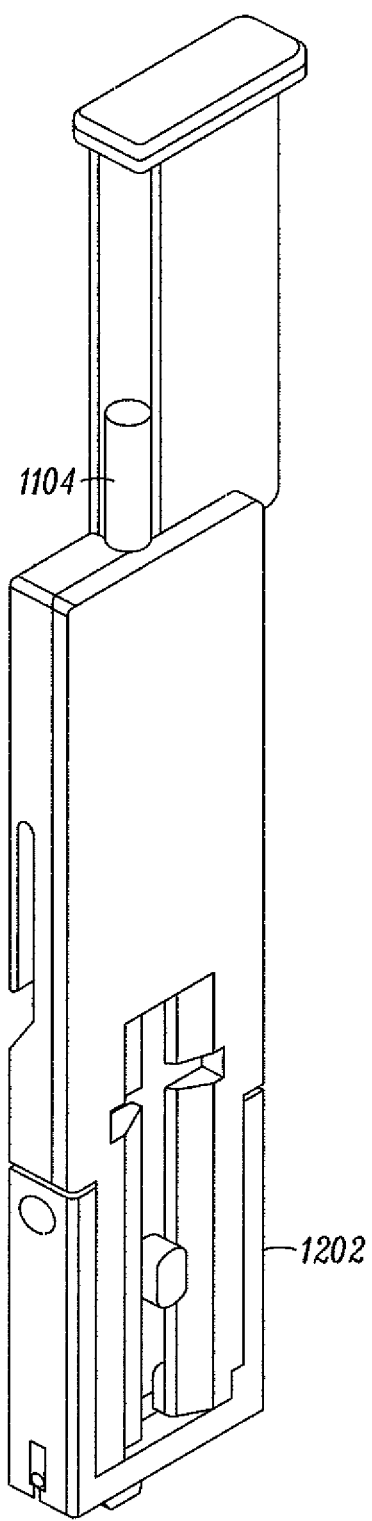
*FIG. 11*  *FIG. 12*

DEVICES FOR ASSEMBLING STRANDS COMPRISING RADIOACTIVE SEEDS

This patent application claims benefit of priority of U.S. Provisional Patent Application No. 60/806,456 entitled, "Devices And Methods For Assembling Strands Of Radioactive Seeds" filed Jun. 30, 2006, and U.S. Provisional Patent Application No. 60/806,457 entitled, "Cartridges, Assemblies, And Methods For Dispensing Items For Strands Of Radioactive Seeds" filed on Jun. 30, 2006.

The present invention is directed generally to medical devices and methods. More particularly, the present invention is directed to cartridges, assemblies, and methods for dispensing items for strands comprising at least one of radioactive seeds, non-radioactive spacers, and connectors, for brachytherapy as well as methods for assembling the strands.

Cancer patients in need of brachytherapy require certain treatment regimens, i.e., a discrete number of radiological seeds arranged in a defined configuration. For example, different numbers of seeds may be required depending on, e.g., the size of the patient, the nature of the tissue in which the seeds are to be implanted, and the type of cancer being treated. In the past, very little (if any) flexibility was provided in assembling strands of brachytherapy seeds. That is, a certain number of seeds were provided to the health care provider in a standard configuration regardless of the needs of the patient. The devices and methods disclosed herein are suitable for treating a number of different types of cancer, especially tissue tumors. For example, the devices and methods can be used to assemble strands for insertion into the prostate gland to treat prostate cancer or the breast to treat breast cancer.

With the advent of specialized brachytherapy, the need has arisen for cartridges, assemblies, and methods for dispensing items for strands of radioactive seeds, connectors and optionally, non-radioactive spacers in accordance with defined, specialized treatment plans. It may also be desired to provide such cartridges, assemblies, and methods with added functionality. Such added functionality may include methods for detecting an empty cartridge and preventing actuating of the empty cartridge, and with the ability to dispense such items without crushing or otherwise deforming them. Such added functionality may also include providing such devices and methods with manual methods for detecting assembly errors to ensure an appropriately assembled device. Such devices and methods could provide for a more efficient brachytherapy procedure, at least because the procedure could be performed in real-time.

In various aspects, the present disclosure is directed to a device for assembling a strand of radioactive seeds. The device may include a carriage portion configured to receive a plurality of cartridges, a selector slidable in a direction perpendicular to the longitudinal axis of the device, and a track configured to receive a plurality of brachytherapy elements. The selector may be operable to select one of the cartridges. An actuator may be configured to eject a seed, connector or, optionally, a spacer from the selected cartridge to the track, and a combiner may be slidable relative to the carriage portion and operable to combine a plurality of seeds and connectors into a single strand.

In some aspects, a device for assembling a strand of radioactive seeds may include a selector assembly operable to select at least one of a radioactive seed, a non-radioactive connector, and a non-radioactive spacer, a track configured to receive a plurality of seeds, connectors, and spacers, an actuator configured to eject either a seed, connector, or a spacer from the selector assembly to said track, and a combiner configured to combine a plurality of seeds, connectors and spacers into a single strand.

According to various aspects, a system for assembling a strand of radioactive seeds may include a housing having a plurality of receptacles for a plurality of the cartridges described above. Each of the cartridges may be associated with one of the receptacles. At least one of the cartridges may contain radioactive seeds, and at least one of the cartridges may contain non-radioactive spacers, and at least one of the cartridges may contain non-radioactive connectors. The track may be configured to receive a plurality of the radioactive seeds, non-radioactive connectors, and non-radioactive spacers, and an actuator may be configured to eject either a seed, a connector, or a spacer from the selected cartridge to the track.

In other aspects, the present disclosure is directed to certain particular aspects of the cartridge described above. A cartridge comprising a housing configured to contain a plurality of like items and a track inside the housing according to the invention is described herein. The track extends in a first direction, and a plunger may be slidable along the track in the first direction and configured to urge the items toward a first end of the housing. The cartridge may include a gate attached to the housing. The gate may be movable between a first position preventing the items from being removed from the housing and a second position allowing one (or more) of the items to be removed from the housing. The gate may be configured to remove the one item(s) from being urged by the plunger.

According to some aspects of the disclosure, a dispensing assembly may comprise the aforementioned cartridge and a rotatable camming member comprising a surface associated with a cam follower. The camming member may be configured to cyclically move the gate from the first position to the second position and allow the gate to move from the second position to the first position.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIG. 11 is a front view of the cartridge of FIG. 9.

FIG. 12 is a perspective view of the cartridge of FIG. 9.

DETAILED DESCRIPTION

According to various embodiments, the devices disclosed herein are used to assemble strands of brachytherapy elements such as, for example, radioactive seeds, non-radioactive spacers, and non-radioactive connectors. Radioactive seeds comprising, e.g., $Pd^{103}$ and $I^{125}$, are well-known and commercially available. For example, $I^{125}$ seeds suitable for brachytherapy are obtainable from Bard Brachytherapy in Carol Stream, Ill. Non-radioactive spacers are typically approximate the size and shape of radioactive seeds. They can be constructed of a variety of different materials such as, for example, aluminum, polypropylene, and bioabsorbable materials. In accordance with certain embodiments, non-radioactive spacers are optionally included in strand assembly. Non-radioactive connectors are configured to join any combination of seeds and optional spacers in end-to-end configurations to form a strand, which in turn is configured for insertion into a brachytherapy needle for delivery to a tumor, such as a tumor in a prostate gland or a breast. Suitable connectors include those disclosed in U.S. Pat. No. 6,010,446 to Peter Grimm, and those disclosed in U.S. Pat. No. 6,969,344 to Drobnik et al. (the disclosures of which are each incorporated by reference herein in their entirety).

An exemplary embodiment of a cartridge and device for assembling strands of brachytherapy elements is illustrated in FIGS. 1-12.

Figure 1:
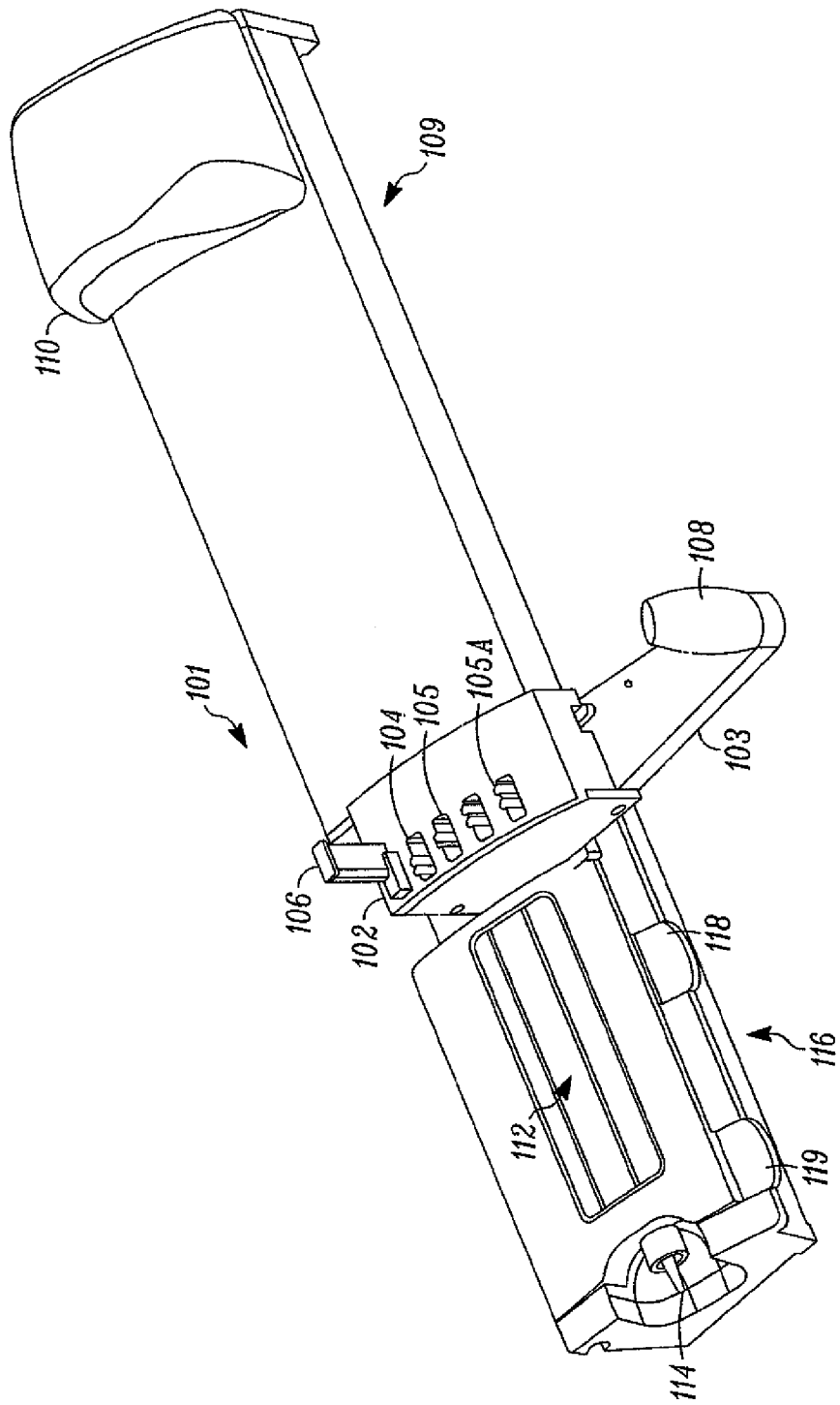
FIG. 1 is a perspective view of an exemplary assembling device in accordance with various aspects of the disclosure.

According to one exemplary aspect of the disclosure, FIG. 1 shows that a device 100 for assembling a strand of radioactive elements may include a housing 101. Housing 101 may include, for example, a carriage portion 102 having a plurality of receptacles 104 configured to receive a corresponding plurality of cartridges 106. Each cartridge 106 may contain one of radioactive seeds, non-radioactive connectors, and non-radioactive spacers (not shown in FIG. 1), and each receptacle may have a different shape to ensure that the cartridges inserted into the respective receptacles each contain the appropriate brachytherapy element. For example, grooves 105 and 105A are complementary to corresponding projections on the cartridges, so that one of five cartridges will fit in only one of five receptacles.

FIG. 1 shows that carriage portion 102 may further include a selector 103 comprising a handle portion 108, slidable in a direction perpendicular to the longitudinal axis of housing 101. Selector 103 may be operable to select one of the cartridges from which brachytherapy elements—e.g., radioactive seeds, non-radioactive connectors, or non-radioactive spacers, may be ejected. The brachytherapy elements may be ejected by an actuator to a track 112 configured to receive a plurality of brachytherapy elements. It should be noted that the element numbers of FIG. 1 are used in some instances in the description that follows. The elements shown in FIG. 1 are intended by these uses.

Figures 2, 3:
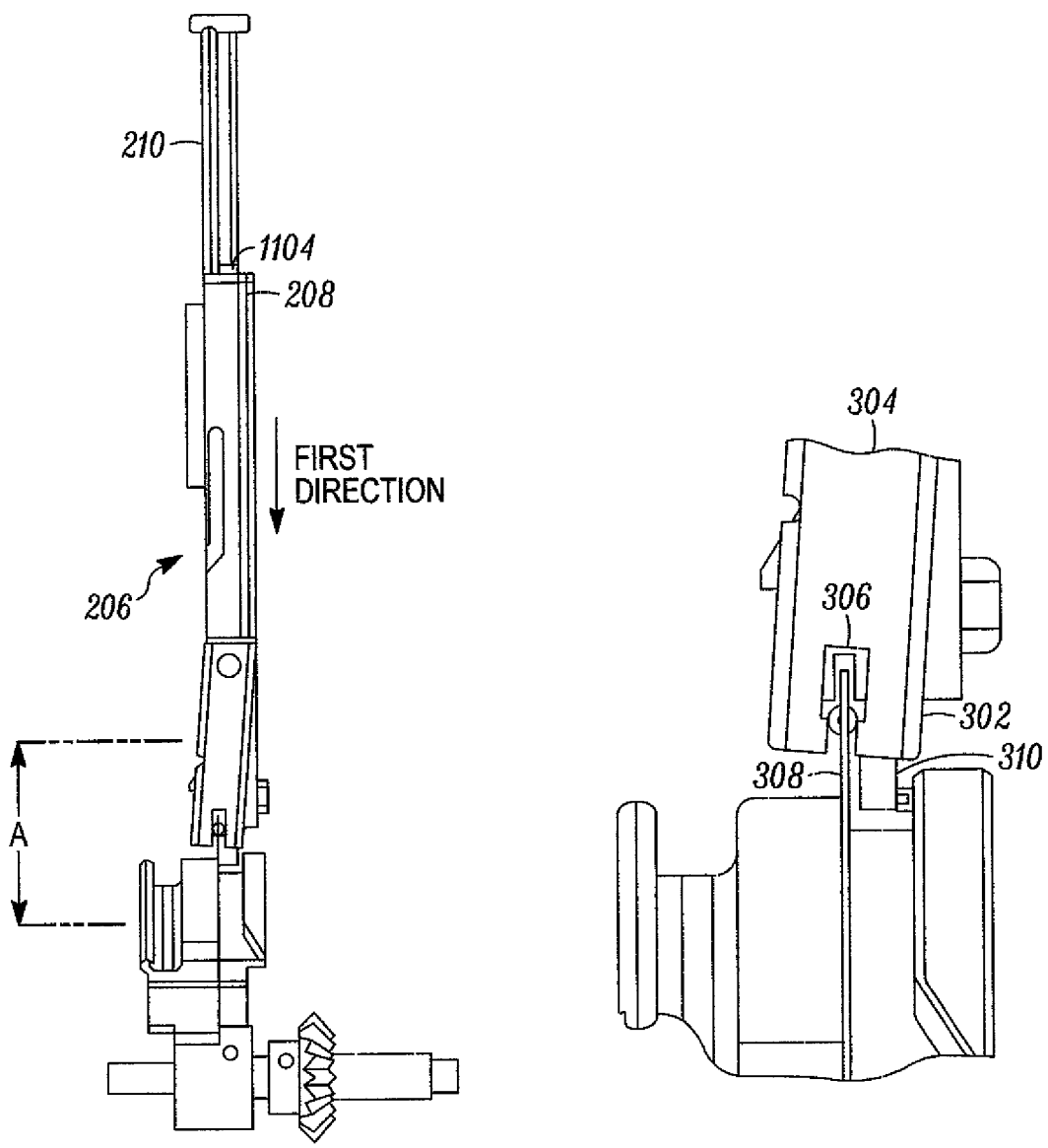
FIG. 2 is a side view of an exemplary part removal assembly and cartridge of the assembling device of FIG. 1.
FIG. 3 is a magnified view of region A of FIG. 2.

FIG. 2 shows a side view of an exemplary part removal assembly and cartridge of the assembling device of FIG. 1. FIG. 2 shows cartridge 206. Cartridge 206 may include a housing 208 configured to contain a plurality of like items and a track inside the housing 208. The track extends in a first direction (as indicated in FIG. 2). A plunger 1104 may be slidable along the track in the first direction and configured to urge the items toward a first end of the housing 208. Plunger 1104 may be protected by housing 208 of cartridge 206. According to some aspects, cartridge 206 may be transparent, translucent, or opaque. Cartridge 206 further comprises a member 210 that indicates the number of brachytherapy elements remaining in the cartridge. Member 210 can comprise graduated markings on the exterior thereof corresponding to the number of brachytherapy elements remaining in the cartridge.

FIG. 3 shows a magnified view of region A of FIG. 2. The cartridge may include a gate 302 attached to the housing. The gate may be movable, for example, pivotally, between a first position preventing the items from being removed from housing 304 and a second position allowing one (or more) of the items to be removed from housing 304. Gate 302 may be configured to remove the one item from being urged by the plunger. In some aspects, gate 302 may be pivotal about an axis substantially perpendicular to the first direction (See, FIGS. 9 and 10).

Cartridge gate slot 306 may be adapted to allow a blade 308 to pass therethrough in order to remove an individual part from the cartridge.

Figure 4:
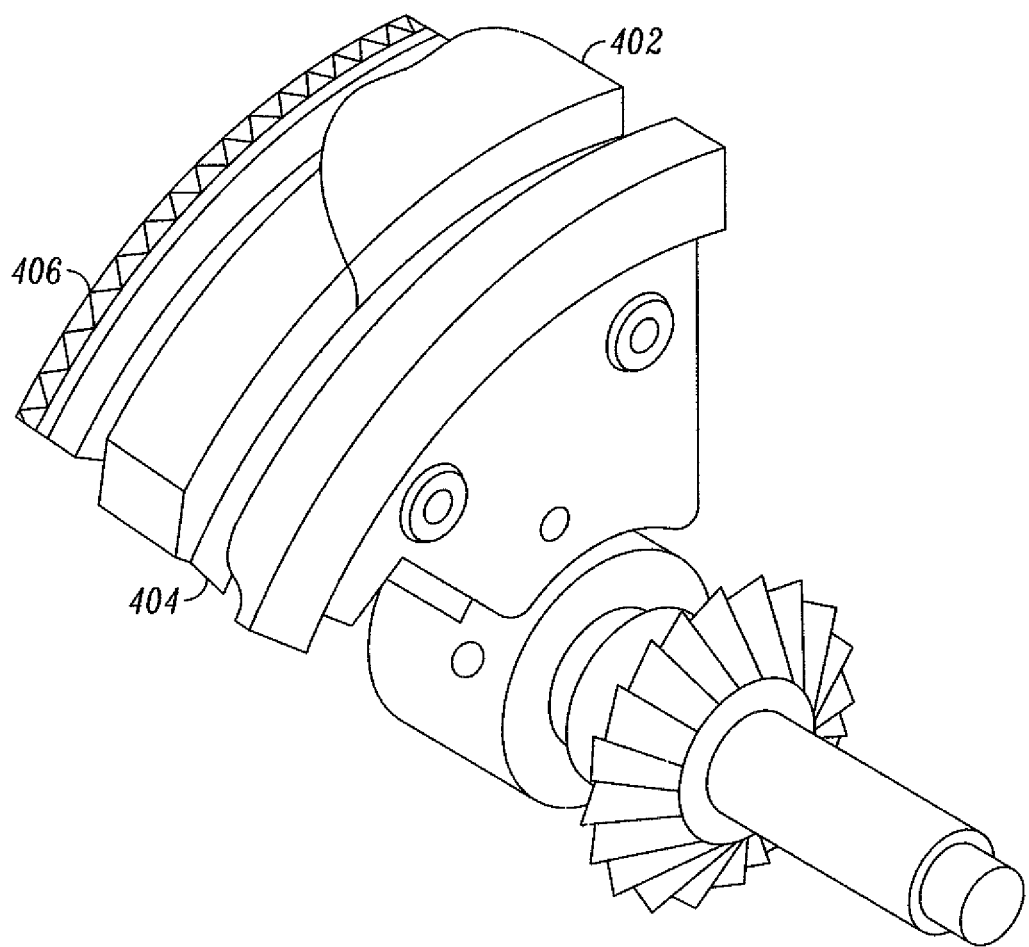
FIG. 4 is a perspective view of the part removal assembly of FIG. 2.

FIG. 4 is a perspective view of the part removal assembly of FIG. 2. FIG. 4 shows an actuator that may comprise a blade removal assembly 400 with a thin blade 402 that removes individual parts from cartridge 206 (shown in FIG. 2). Assembly 400 may include a rotatable camming member 404 that is configured to cyclically urge a cam follower extending from the gate of each cartridge (see, e.g., 310 in FIG. 3).

The camming member 404/cam follower assembly (the blade 402 may be considered associated with the cam follower because it depends on the movement of the cam; see below for more detail about blade 402) may cause a gate associated with a selected cartridge to move between a first, closed position and a second, open position. In moving from the first position to the second position, the gate may remove a single part from a plurality of parts out of the path of the plunger (see FIG. 2 for "first direction" of the plunger). FIG. 4 also shows a cartridge carriage motion locking track 406 that locks the motion of the cartridge carriage.

The plurality of parts may be integrally connected with the cartridge, and, when the gate returns to its previous position, the gate may sever such connection of the single part. The gate may further include a slot (see cartridge gate slot 306 in FIG. 3) for holding the removed part such that the part is no longer being urged by the plunger. The slot may extend through the gate in a direction substantially perpendicular to the first direction.

The blade removal assembly may further include a pusher 402, for example, a thin blade, associated with the cam follower and configured to remove the single part from slot 306 in the selected cartridge. The part may be either a seed or a spacer depending on which cartridge is selected. Plunger 1104 may be structured and arranged to prevent operation of the actuator when no parts remain in a cartridge, thus providing an indication of an empty cartridge and functioning as a lockout mechanism to prevent a blank dispensing.

Device 100 may further include a combiner housing 109 (see FIG. 1) slidable relative to carriage portion 102. Combiner housing 109 may comprise a compression handle 110 operable to combine, via an attached stylet (not shown), a plurality of seeds, connectors and optional spacers in track 112 into a single strand.

Figure 5A:
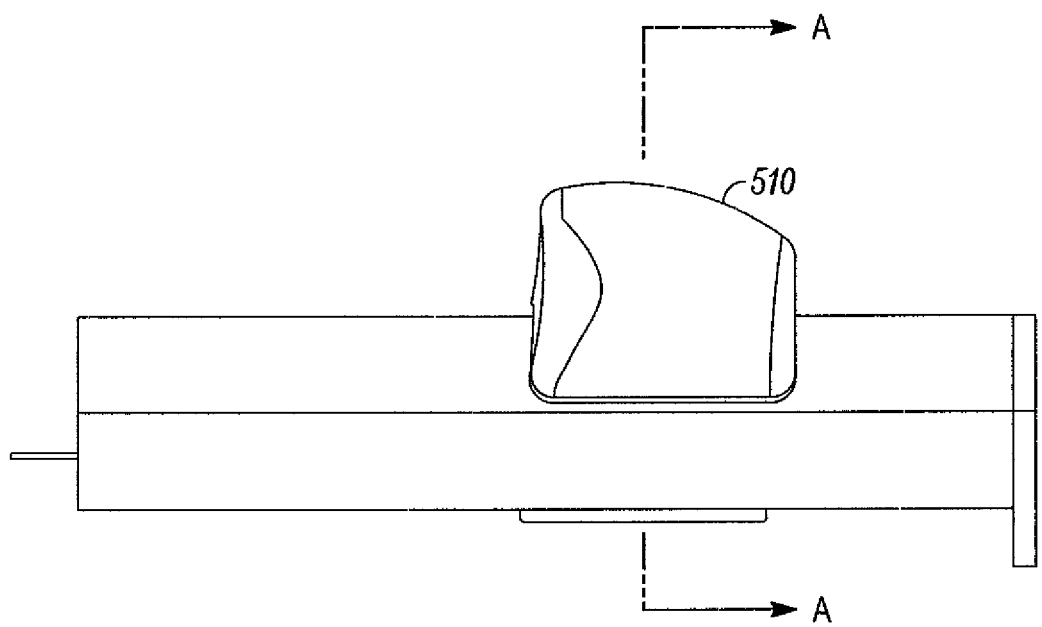
FIG. 5A is a side view of an exemplary compression mechanism of the assembling device of FIG. 1.
Figure 5B:
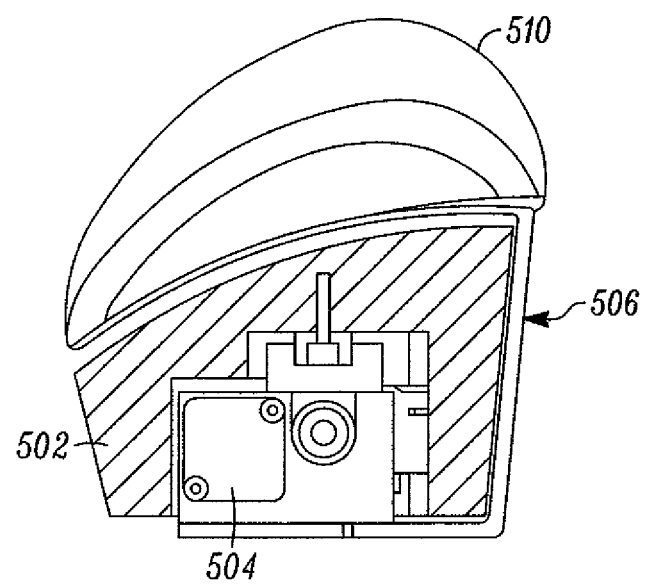
FIG. 5B is a partially cut-away end view taken from line A-A of the exemplary compression mechanism of the assembling device of FIG. 5A.

FIG. 5A shows a slidable handle 510. FIG. 5B shows a side view taken from line A-A in FIG. 5A. FIG. 5B shows structural support member 502, magnetic material 504 (behind a plastic cover) and handle connection 506 that connects handle 510 to be able to release the internal mechanics of the combiner housing 109.

Figure 6:
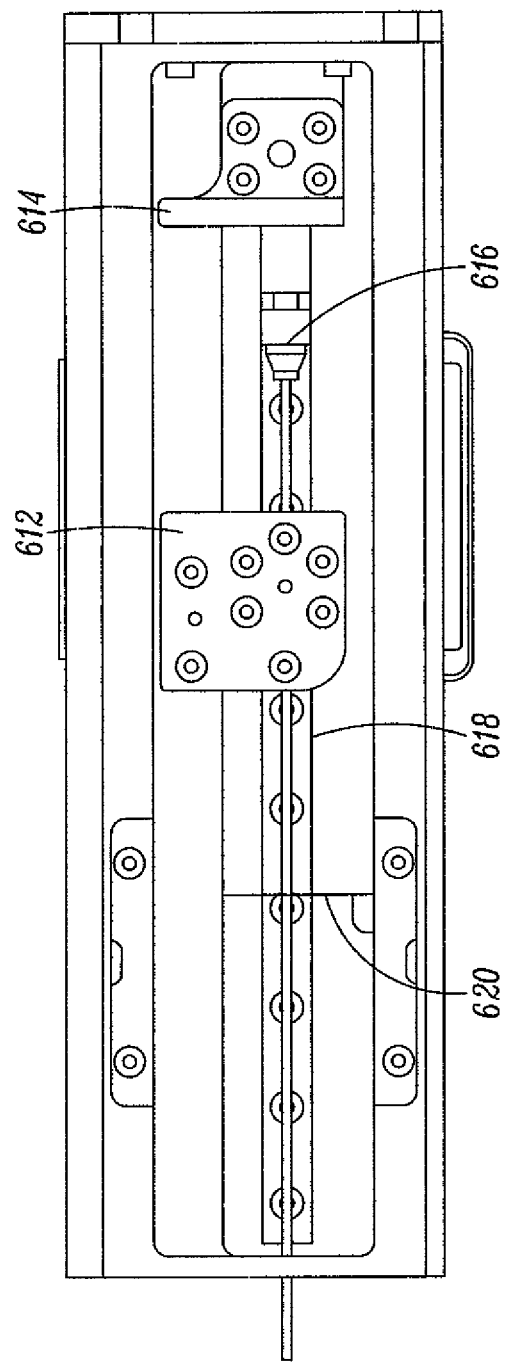
FIG. 6 is a cut-away bottom view of the compression mechanism of FIG. 5.

FIG. 6 shows a cut-away bottom view of the compression mechanism of FIGS. 5A and 5B. The compression force of combiner housing 109 may be delivered by decoupling magnets, including permanent—i.e., fixed with respect to the movement of handle 510—magnet 612 and magnetic material 614, so as to prevent application of excessive force to the brachytherapy elements during compression, which could result in rupturing those elements. Alternatively, a mechanical friction force may be used. The combiner may also be operable to urge the combined strand into a needle via a needle adaptor (see element 114 in FIG. 1) associated with track 112 shown in FIG. 1. Needle adaptor 114 may extend from to the exterior of the device, and may be complementary to the hub of a brachytherapy needle.

The device may include a stylet 616 associated with the combiner. The combiner may be configured to urge the strand into a needle (not shown) via the stylet 616. Stylet 616 may be pushed along linear guide rail 618. Stylet 616 may be prevented from buckling by stylet buckling support 620.

The device may include a lockout mechanism configured to prevent operation of the actuator when a selected cartridge is empty. This feature may be in addition to, or as an alternative to, a visual indicator associated with each cartridge.

In operation, a user may place up to five cartridges—one into each of the five receptacles (see FIG. 1, elements 104)—in the carriage portion 102 of device 100. One cartridge can include radioactive seeds, the second can include non-radioactive spacers, and three cartridges can include non-radioactive connectors of various lengths and configurations. Carriage portion 102 may then be moved by sliding carriage handle 108 in a direction perpendicular to the longitudinal dimension of the device. Carriage portion 102 may be moved so as to align a selected one of the five cartridges with a removal assembly 116. Device 100 may have an indicator to aid with such alignment.

By pressing release button 118 on device 100, an actuator, for example, a blade removal assembly (see, FIGS. 2-4), interacts with gate 302 of the selected cartridge and prepares one part (e.g., a radioactive seed, non-radioactive connector, or non-radioactive spacer) for removal from cartridge 102. In one exemplary embodiment, such preparation may comprise shearing a single part from a plurality of interconnected parts. The actuator may then remove the part from the selected cartridge and advance it into track 112 of device 100. This alignment and removal procedure may be repeated until the operator has positioned all of the parts for a desired strand into the track.

Figure 7:
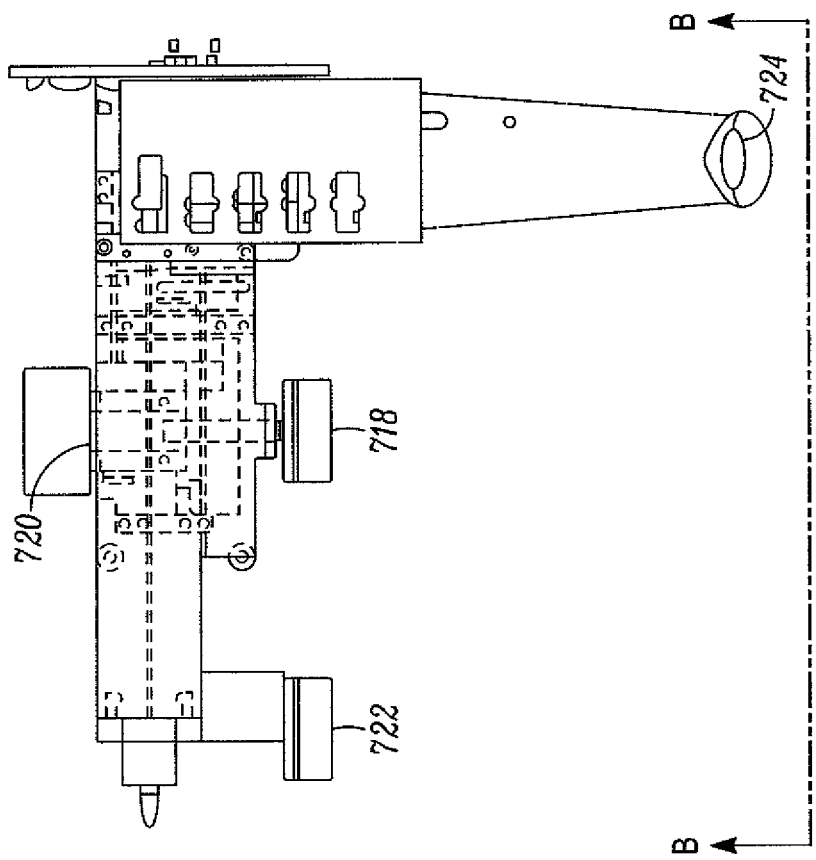
FIG. 7 is a top view of an exemplary carriage assembly of the assembling device of FIG. 1.

FIG. 7 shows a top view of an exemplary carriage assembly of the assembling device of FIG. 1. Release button 718 which may include a magnetic clutch 720 structured and arranged to disengage when a cartridge is emptied in order to alert the operator and prevent the final strand from being misassembled. Gate button 722 and handle 724 are also shown in FIG. 7.

Figure 8:
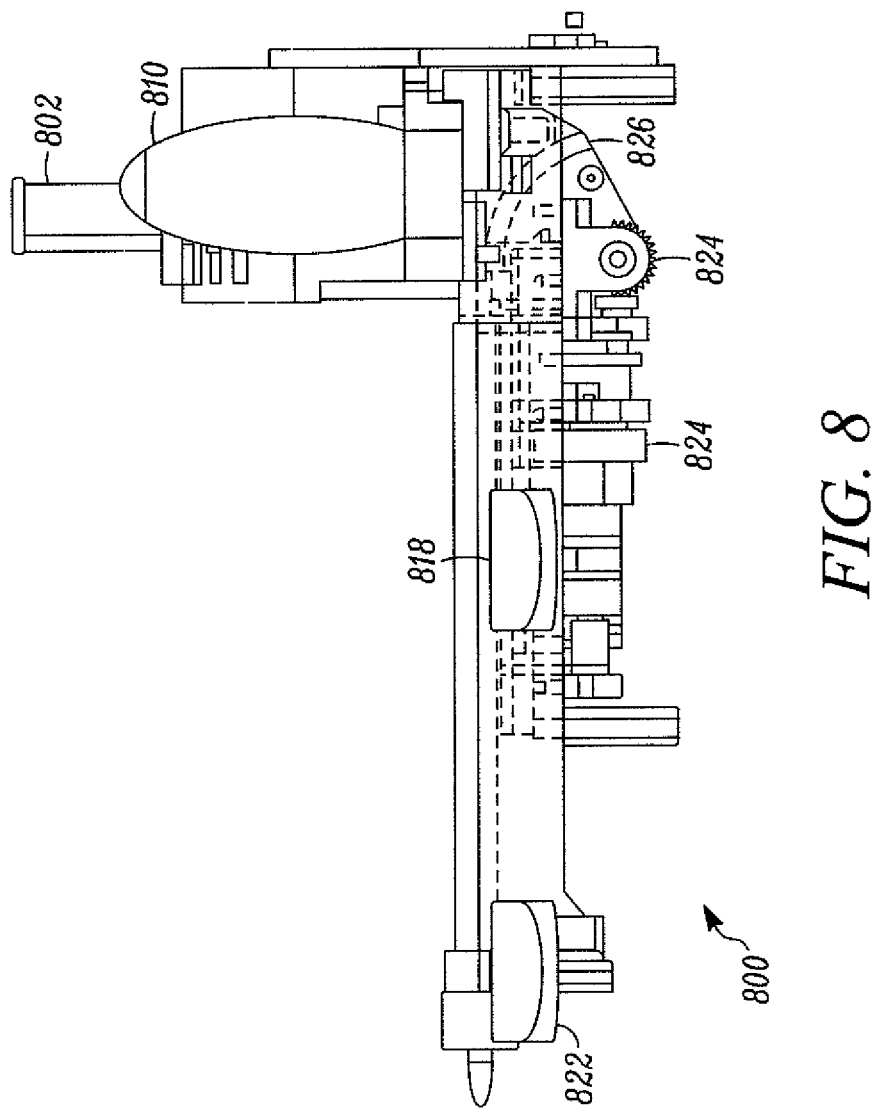
FIG. 8 is a side view of the exemplary carriage assembly of the assembling device of FIG. 7.

FIG. 8 shows a side view of the exemplary carriage assembly 800 of the assembling device in FIG. 7 taken from line B-B. Carriage assembly 800 includes an inserted brachytherapy element cartridge 802, handle 810, release button 818, gate button 822, motion transfer gearing 824 and part removal assembly 826. Motion transfer gearing 824 acts to transform actuation of 818 into cyclical motion of part removal assembly 826. The cyclical motion of assembly 826 removes an individual part from the gate and places it in track 112.

Once all of the seeds and spacers are positioned in track 112 as desired, the operator may slide combiner 110 toward track 112 to form the seeds and spacers into a strand. For example, the combiner may include a compression handle which is attached to a stylet, (see element 510 in FIG. 5) and applied force compresses the stylet into the brachytherapy elements to form a strand. This compression occurs when stylet (see 616 in FIG. 6) is engaged.

A needle (not shown) may be attached to needle adaptor 114. Gate button 119 (FIG. 1) may then be held in the downward position and handle 510 slid toward track 112 to move the strand into the needle.

At any point during operation, the operator may inspect a cartridge 106 by simply removing the cartridge 106 from its receptacle 104 in the carriage portion 102. Upon removal from receptacle 104, the cartridge gate (see, element 302 in FIG. 3) keeps the contents of the cartridge safely contained.

Figure 9:
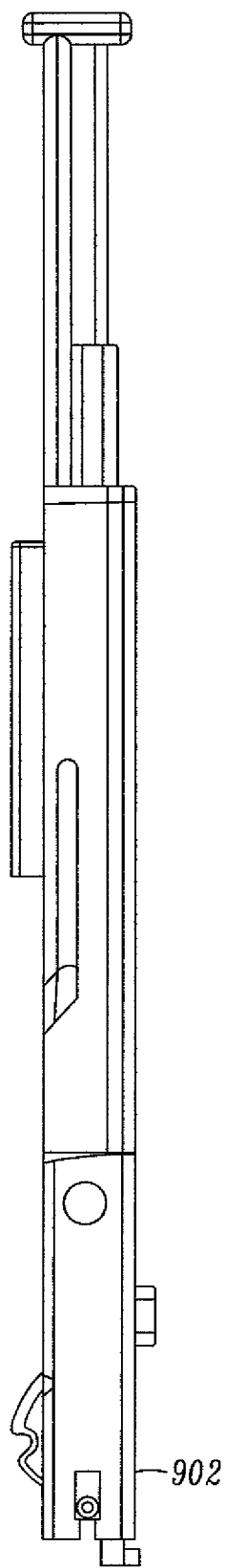
FIG. 9 is a side view of an exemplary cartridge in accordance with various aspects of the disclosure.

FIG. 9 shows a side view of gate 902 in a closed position.

Figure 10:
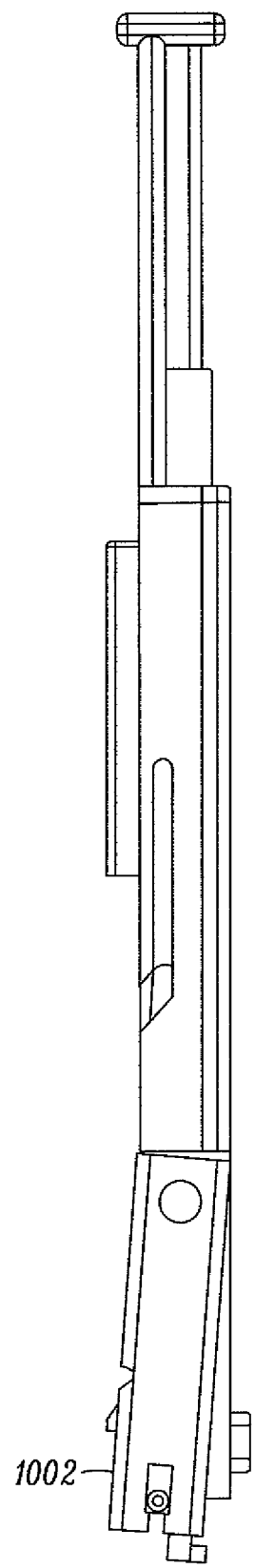
FIG. 10 is a side view of the cartridge of FIG. 9 in a different configuration.

FIG. 10 shows aside view of gate 1002 in an open position.

FIG. 11 shows a front view of a cartridge 1102. When a cartridge is empty, a plunger 1104 in cartridge 1102 may advance down into the cartridge gate, causing the cartridge gate to be immobilized. If the release button is pressed when the actuator is aligned with an empty cartridge, the immobilized gate prevents the actuator from operating. This positive stop, or lockout, prevents the operator from proceeding even if the operator doesn't notice the visual indicator on the cartridge. As a result, the device is prevented from assembling an incorrect strand configuration.

FIG. 12 shows a perspective view of a cartridge 1202 according to the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A device for assembling a strand of radioactive seeds, comprising:
    a carriage portion configured to receive a plurality of cartridges;
    a selector slidable relative to the longitudinal axis of the device, the selector being operable to select one of said cartridges;
    a track configured to receive a plurality of radioactive seeds, non-radioactive connectors, and non-radioactive spacers;
    an actuator configured to eject one of a seed, connector, and a spacer from said selected cartridge to said track;
    a lockout mechanism configured to prevent operation of the actuator when a selected cartridge is empty;
    a combiner slidable relative to the carriage portion, said combiner being operable to combine a plurality of seeds, connectors, and spacers into a single strand; and
    a stylet associated with said combiner, the stylet separate from the actuator,
    wherein the combiner comprises decoupling magnets to prevent application of excessive compression force that could result in rupturing at least one of the radioactive seeds, non-radioactive connectors, and non-radioactive spacers.

2. The device of claim 1, wherein said combiner is operable to urge said strand into a needle via said stylet.

3. The device of claim 2, further comprising a needle adaptor associated with said track.

4. A device for assembling a strand of radioactive seeds, comprising:

a selector assembly operable to select one of radioactive seeds, non-radioactive connectors, and non-radioactive spacers, wherein:

the selector assembly includes a cartridge containing a plurality of seeds, connectors, or spacers, the cartridge including a gate movable between a first position preventing any of the plurality seeds, connectors, or spacers from being removed from the cartridge and a second position allowing at least one of the plurality of seeds, connectors, or spacers to be removed from the cartridge; and the plurality of seeds, connectors, or spacers are urged by a plunger of the cartridge along a path extending substantially in a first direction, and the gate is configured to remove the at least one of the plurality of seeds, connectors, or spacers from said path as the gate moves to the second position;

a track configured to receive a plurality of said seeds, connectors, and/or spacers;

an actuator configured to eject one of a seed, connector, and a spacer from said selector assembly to said track;

a combiner configured to combine a plurality of seeds, connectors, and/or spacers into a single strand, wherein the combiner includes decoupling magnets to prevent application of excessive compression force that might result in rupturing at least one of the radioactive seeds, non-radioactive connectors, and/or non-radioactive spacers; and a stylet associated with said combiner, said combiner being configured to urge said strand into a needle via the stylet, the stylet separate from the actuator.

5. The device of claim 4, wherein the actuator further comprises a rotatable camming member comprising a surface associated with a cam follower, said camming member being configured to cyclically move the gate from the first position to the second position and allow the gate to move from the second position to the first position.

6. The device of claim 4, wherein the actuator further comprises a pusher configured to eject the one of a seed, connector, and a spacer from the cartridge to the track, the pusher different from the stylet.

7. The device of claim 6, wherein the gate includes a slot extending through at least a portion of the gate, the slot being configured to hold the removed at least one of the plurality of seeds, connectors, or spacers, and wherein the pusher comprises a blade, said blade being configured to move through the slot and remove the at least one of the plurality of seeds, connectors, or spacers from the cartridge.

8. The device of claim 4, wherein the plurality of seeds, connectors, or spacers are integrally connected to one another, and the gate is configured to sever the connection between the at least one of the plurality of seeds, connectors, or spacers and a remainder of the plurality of seeds, connectors, or spacers.

9. A device for assembling a strand of radioactive seeds, comprising:

a selector assembly operable to select one of radioactive seeds, non-radioactive connectors, and non-radioactive spacers, wherein the selector assembly includes a cartridge containing a plurality of seeds, connectors, or spacers, the cartridge including a gate movable between a first position preventing any of the plurality seeds, connectors, or spacers from being removed from the cartridge and a second position allowing at least one of the plurality of seeds, connectors, or spacers to be removed from the cartridge;

a track configured to receive a plurality of said seeds, connectors, and/or spacers;

an actuator configured to eject one of a seed, connector, and a spacer from said selector assembly to said track, wherein the actuator includes a rotatable camming member comprising a surface associated with a cam follower, said camming member being configured to cyclically move the gate from the first position to the second position and allow the gate to move from the second position to the first position;

a combiner configured to combine a plurality of seeds, connectors, and/or spacers into a single strand, wherein the combiner comprises decoupling magnets to prevent application of excessive compression force that might result in rupturing at least one of the radioactive seeds, non-radioactive connectors, and/or non-radioactive spacers; and a stylet associated with said combiner, said combiner being configured to urge said strand into a needle via the stylet, the stylet separate from the actuator.

10. The device of claim 9, wherein the actuator further includes a pusher configured to eject the one of a seed, connector, and a spacer from the cartridge to the track, the pusher different from the stylet.

11. The device of claim 10, wherein the gate includes a slot extending through at least a portion of the gate, the slot being configured to hold the removed at least one of the plurality of seeds, connectors, or spacers, and wherein the pusher comprises a blade, said blade being configured to move through the slot and remove the at least one of the plurality of seeds, connectors, or spacers from the cartridge.

12. The device of claim 9, wherein the plurality of seeds, connectors, or spacers are integrally connected to one another, and the gate is configured to sever the connection between the at least one of the plurality of seeds, connectors, or spacers and a remainder of the plurality of seeds, connectors, or spacers.

13. A device for assembling a strand of radioactive seeds, comprising:

a selector assembly operable to select one of radioactive seeds, non-radioactive connectors, and non-radioactive spacers, wherein:

the selector assembly includes a cartridge containing a plurality of seeds, connectors, or spacers, the cartridge including a gate movable between a first position preventing any of the plurality seeds, connectors, or spacers from being removed from the cartridge and a second position allowing at least one of the plurality of seeds, connectors, or spacers to be removed from the cartridge; and the plurality of seeds, connectors, or spacers are integrally connected to one another, and the gate is configured to sever the connection between the at least one of the plurality of seeds, connectors, or spacers and a remainder of the plurality of seeds, connectors, or spacers;

a track configured to receive a plurality of said seeds, connectors, and/or spacers;

an actuator configured to eject one of a seed, connector, and a spacer from said selector assembly to said track;

a combiner configured to combine a plurality of seeds, connectors, and/or spacers into a single strand, wherein the combiner includes decoupling magnets to prevent application of excessive compression force that might result in rupturing at least one of the radioactive seeds, non-radioactive connectors, and/or non-radioactive spacers; and a stylet associated with said combiner, said combiner being configured to urge said strand into a needle via the stylet, the stylet separate from the actuator.

14. The device of claim 13, wherein the actuator includes a rotatable camming member comprising a surface associated with a cam follower, said camming member being configured to cyclically move the gate from the first position to the second position and allow the gate to move from the second position to the first position.

15. The device of claim 13, wherein the actuator includes a pusher configured to eject the one of a seed, connector, and a spacer from the cartridge to the track, the pusher different from the stylet.

16. The device of claim 15, wherein the gate includes a slot extending through at least a portion of the gate, the slot being configured to hold the removed at least one of the plurality of seeds, connectors, or spacers, and wherein the pusher comprises a blade, said blade being configured to move through the slot and remove the at least one of the plurality of seeds, connectors, or spacers from the cartridge.

* * * * *